US011317961B2

(12) United States Patent
Luzon et al.

(10) Patent No.: US 11,317,961 B2
(45) Date of Patent: May 3, 2022

(54) SKIN TREATMENT DEVICE (71) Applicant: El Global Trade Ltd., Netanya (IL)

(72) Inventors: Josef Luzon, Bet Yehoshua (IL); Martin Gurovich, Tel Aviv (IL)

(73) Assignee: EL GLOBAL TRADE LTD., Netanya (IL)

( * ) Notice: Subject to any disclaimer, the term of this patent is extended or adjusted under 35 U.S.C. 154(b) by 349 days.

(21) Appl. No.: 16/508,549

(22) Filed: Jul. 11, 2019

(65) Prior Publication Data
US 2019/0328447 A1 Oct. 31, 2019

Related U.S. Application Data (63) Continuation-in-part of application No. 13/609,428, filed on Sep. 11, 2012, now abandoned.

(51) Int. Cl.
*A61B 18/00* (2006.01)
*A61B 18/14* (2006.01)
*A61B 18/12* (2006.01)

(52) U.S. Cl.
CPC ...... *A61B 18/14* (2013.01); *A61B 2018/0047* (2013.01); *A61B 2018/00184* (2013.01); *A61B 2018/00642* (2013.01); *A61B 2018/00702* (2013.01); *A61B 2018/00791* (2013.01); *A61B 2018/1226* (2013.01)

(58) Field of Classification Search
CPC .......... A61B 18/14; A61B 2018/00184; A61B 2018/0047; A61B 2018/1226; A61B 2018/00702; A61B 2018/00791; A61B 2018/00642; A61B 2018/00208; A61B 2018/00666
See application file for complete search history.

(56) References Cited

U.S. PATENT DOCUMENTS

| 2,912,976 | A | * | 11/1959 | Grund ................... A61H 13/00 |
| | | | | 601/140 |
| 5,536,267 | A | | 7/1996 | Edwards et al. |
| 6,254,598 | B1 | | 7/2001 | Edwards et al. |
| 6,256,540 | B1 | | 7/2001 | Panescu et al. |
| 6,471,699 | B1 | | 10/2002 | Fleischman et al. |

(Continued)

FOREIGN PATENT DOCUMENTS

| CN | 101610736 A | 12/2009 |
| JP | 2011194176 A * | 10/2011 |

(Continued)

OTHER PUBLICATIONS

China Office Action issued for application No. 201280070863.5, dated Jul. 1, 2015.

(Continued)

*Primary Examiner* — Joanne M Hoffman
*Assistant Examiner* — Yasamin Ekrami
(74) *Attorney, Agent, or Firm* — Dorsey & Whitney LLP (57) ABSTRACT

A device for treating skin includes two mechanical fingers for placement in contact with the skin. At least one of the fingers is moveable so as to change a separation distance between the fingers. The fingers are configured to concurrently conduct a generated radiofrequency electromagnetic signal to the skin so as to cause an electrical current to flow through the skin at a depth that corresponds to the separation distance.

20 Claims, 5 Drawing Sheets

(56) References Cited

U.S. PATENT DOCUMENTS

| | | |
|---|---|---|
| 6,638,275 B1 | 10/2003 | Mcgaffigan et al. |
| 6,641,580 B1 | 11/2003 | Edwards et al. |
| 6,662,054 B2 | 12/2003 | Kreindel et al. |
| 8,506,506 B2 | 8/2013 | Nebrigic et al. |
| 2002/0128641 A1 | 9/2002 | Underwood et al. |
| 2004/0236255 A1* | 11/2004 | Cook ............... A61N 1/328 601/15 |
| 2005/0192520 A1 | 9/2005 | Morita et al. |
| 2006/0036300 A1 | 2/2006 | Kreindel |
| 2006/0064085 A1 | 3/2006 | Schechter et al. |
| 2007/0055171 A1 | 3/2007 | Fraden |
| 2007/0179490 A1 | 8/2007 | Azar et al. |
| 2008/0183251 A1* | 7/2008 | Azar ............... A61B 18/14 607/101 |
| 2008/0200861 A1 | 8/2008 | Shalev et al. |
| 2009/0131932 A1 | 5/2009 | Vakharia et al. |
| 2010/0036298 A1* | 2/2010 | Fuster ............... A61H 7/007 601/133 |
| 2010/0179455 A1 | 7/2010 | Cinco et al. |
| 2010/0210993 A1 | 8/2010 | Flyash et al. |
| 2010/0228243 A1 | 9/2010 | Mehta |
| 2014/0288473 A1* | 9/2014 | Matsushita ....... A61H 15/0085 601/137 |

FOREIGN PATENT DOCUMENTS

| | | |
|---|---|---|
| JP | 2011194176 A | 10/2011 |
| WO | 9116859 A1 | 11/1991 |
| WO | 2011058565 A2 | 5/2011 |

OTHER PUBLICATIONS

European Search Report issued for application No. 12863623.0, dated Aug. 14, 2015.
International Preliminary Report on Patentability of International Application No. PCT/IL2012/050529 dated Jul. 10, 2014.
International Search Report for Application No. PCT/IL2012/050529, dated Apr. 23, 2013.
U.S. Appl. No. 13/609,428, filed Sep. 11, 2012.
U.S. Appl. No. 62/580,687, filed Dec. 28, 2011.

* cited by examiner

SKIN TREATMENT DEVICE

CROSS REFERENCE TO RELATED APPLICATIONS

This application is a continuation-in-part of U.S. patent application Ser. No. 13/609,428 filed on Sep. 11, 2012, which is incorporated herein, in its entirety, by this reference.

FIELD OF THE INVENTION

The present invention relates to a skin treatment device.

BACKGROUND OF THE INVENTION

One goal of various beauty treatments is tightening of the skin so as to give the skin a smooth and non-wrinkled appearance. Various treatments for tightening the skin have been developed and applied over the centuries.

Massaging the skin has been considered to lead to skin tightening. Application of massage is claimed by proponents to benefit the skin by stimulating the vascular system, as well as by promoting the drainage of lymph from skin tissue. In addition to manual massage, various mechanical devices have been developed to massage the skin in a consistent and repeatable manner.

Other treatments for the skin are based on selective electro-thermolysis. In selective electro-thermolysis, layers of the skin are subjected to heating. In particular, delivery of radiofrequency (RF) electromagnetic energy to layers of the skin has been promoted as an effective way of heating the skin in a controlled manner for treatment purposes. Application of RF energy as a skin treatment has been described as increasing cell metabolism rates, increasing blood flow to the skin, causing adipocyte necrosis (shrinking of fat cells), and as stimulating remodeling of collagen.

It is an object of embodiments of the present invention to provide a device for effective treatment of the skin.

Other aims and advantages of embodiments of the present invention will become apparent after reading the present invention and reviewing the accompanying drawings.

SUMMARY OF THE INVENTION

There is provided, in accordance with some embodiments of the present invention, a device including a housing having an opening, a periphery of the opening comprising a connection portion, the housing enclosing a generator for generating a radiofrequency electromagnetic signal and a controller for controlling the generator. The device further including two mechanical arms having a space therebetween, each of the two mechanical arms comprising a respective distal end projecting outwards from the opening of the housing, the two mechanical arms being rotatable to change a separation distance between the distal ends of the two mechanical arms between a maximal separation distance and a minimal separation distance, a first one of the two mechanical arms being rotatable about a first rotation axis and a second one of the two mechanical arms being rotatable about a second rotation axis laterally spaced from the first rotation axis, the two mechanical arms being configured to rotate periodically back-and-forth about the respective first and second rotation axis thereof so that distal ends thereof move along an arcuate path. The device further including two mechanical fingers, each located at the distal end of a respective mechanical arm, a respective periphery of each of the two mechanical fingers comprising a sleeve connection portion, each of the two mechanical fingers being configured to conduct the generated radiofrequency electromagnetic signal to a surface in contact with the two mechanical fingers, at least one of the two mechanical fingers including a temperature sensor to sense a temperature of the surface. The device further including a flexible sleeve comprising a waist portion, two leg portions extending from the waist portion, and a depression between the two leg portions, the waist portion comprising a housing connection portion corresponding to the connection portion of the opening of the housing and connected thereto, each of the two leg portions comprising a finger connection portion corresponding to the respective sleeve connection portion of the two mechanical fingers and connected thereto, each of the two leg portions at least partially surrounding a respective mechanical arm and the two leg portions meet each other in the space between the two mechanical arms, thereby forming the depression.

Furthermore, in accordance with some embodiments of the present invention, each of the two mechanical fingers includes a respective temperature sensor to sense the temperature of the surface at the corresponding contact point of the mechanical finger with the skin, simultaneously while the mechanical fingers conduct the generated radiofrequency electromagnetic signal to the contact points.

Furthermore, in accordance with some embodiments of the present invention, the device is used for treating skin, the two mechanical fingers for placement in contact with the skin, the fingers being configured to concurrently conduct a generated radiofrequency electromagnetic signal to the skin so as to cause an electrical current to flow through the skin at a depth that corresponds to the separation distance.

Furthermore, in accordance with some embodiments of the present invention, the device is shaped so as to be held by a single hand.

Furthermore, in accordance with some embodiments of the present invention, the device includes a motor and transmission for moving said at least one of the arms, and thereby the fingers.

Furthermore, in accordance with some embodiments of the present invention, the transmission includes a cam that is rotatable by the motor for changing a distance between the fingers located at the distal ends of the arms.

Furthermore, in accordance with some embodiments of the present invention, the cam is located so as to contact the arm at a point between the distal end of the arm and the axis of the arm.

Furthermore, in accordance with some embodiments of the present invention, the device includes a spring for exerting an inward torque on at least one of the arms.

Furthermore, in accordance with some embodiments of the present invention, the device includes a controller for controlling operation of the motor.

Furthermore, in accordance with some embodiments of the present invention, the device includes a temperature sensor for sensing a temperature of the skin.

Furthermore, in accordance with some embodiments of the present invention, the temperature sensor is embedded in at least one of the fingers.

Furthermore, in accordance with some embodiments of the present invention, the radiofrequency electromagnetic signal is generated in accordance with the sensed temperature.

Furthermore, in accordance with some embodiments of the present invention, the device is configured to interrupt generation of the radiofrequency electromagnetic signal if the sensed temperature exceeds a threshold temperature.

Furthermore, in accordance with some embodiments of the present invention, the device includes a control for operation by a user.

Furthermore, in accordance with some embodiments of the present invention, the device includes an indicator for indicating a status of the device.

Furthermore, in accordance with some embodiments of the present invention, the device includes a power supply.

Furthermore, in accordance with some embodiments of the present invention, the power supply includes a rechargeable battery or a replaceable battery.

Furthermore, in accordance with some embodiments of the present invention, each leg portion moves along with the respective mechanical arm, thereby at least partially deforming the flexible sleeve and changing at least one dimension of the depression.

Furthermore, in accordance with some embodiments of the present invention, the flexible sleeve is configured to seal a space between the mechanical fingers and the opening of the housing.

Furthermore, in accordance with some embodiments of the present invention, the leg portions and the waist portion are integrally formed.

Furthermore, in accordance with some embodiments of the present invention, the leg portions and the waist portion are different elements articulated to each other.

Furthermore, in accordance with some embodiments of the present invention, the leg portions define respective hollows and the respective mechanical arms pass therethrough.

Furthermore, in accordance with some embodiments of the present invention, an external surface of the flexible sleeve forms a continuous surface along with an external surface of the housing and external surfaces of the two mechanical fingers.

Furthermore, in accordance with some embodiments of the present invention, the generator is configured to continuously vary a frequency of the radiofrequency electromagnetic signal in coordination with the changing separation distance.

There is further provided, in accordance with some embodiments of the present invention, a method for treating skin, the method including: placing against the skin at least two fingers of a skin treatment device; controlling operation of the device so as to move at least one of the fingers such that a separation distance between the fingers is changed by the motion so as to massage the skin in the vicinity of the fingers; and controlling operation of the device such that a radiofrequency electromagnetic signal is applied to the skin via the fingers so as to cause a radiofrequency electrical current to be conducted between the fingers by a layer of the skin at a depth that corresponds to the separation distance so as to heat at least that layer of the skin.

Furthermore, in accordance with some embodiments of the present invention, the method includes determining the separation distance and adjusting a characteristic of the applied radiofrequency electromagnetic signal in accordance with the determined so as to control the depth of the layer that is heated.

Furthermore, in accordance with some embodiments of the present invention, the characteristic includes a frequency of the generated radiofrequency electromagnetic signal.

Furthermore, in accordance with some embodiments of the present invention, the method includes concurrently continuously moving the device over the skin.

Furthermore, in accordance with some embodiments of the present invention, the method includes sensing a temperature of the skin and adjusting the applied radiofrequency electromagnetic signal in accordance with the sensed temperature.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

In the following detailed description, numerous specific details are set forth in order to provide a thorough understanding of embodiments of the invention. However, it will be understood by those of ordinary skill in the art that the invention may be practiced without these specific details. In other instances, well-known methods, procedures, components, modules, units and/or circuits have not been described in detail so as not to obscure the invention.

In accordance with embodiments of the present invention, a skin treatment device includes two or more radiofrequency (RF) electrodes. Each radiofrequency electrode is incorporated in a mechanical finger. One or more of the mechanical fingers is movable with a back-and-forth motion.

The skin treatment device may include a mechanism for coordinated movement of two or more of the mechanical fingers. For example, the coordinated movement may enable distal ends of two mechanical fingers to alternately approach and recede from one another. The motion may be repetitive or periodic.

A frequency or speed of the motion of a mechanical finger may be adjustable. Similarly, a distance through which a mechanical finger is moved during the course of the motion (e.g. amplitude of the motion) may be adjustable.

Alternatively to coordinated motion of two or more mechanical fingers, one mechanical finger may be moved relative to one or more stationary neighboring mechanical fingers. Reference herein to motion of mechanical fingers should be understood as referring to motion of the mechanical fingers relative to one another, regardless of how many of the mechanical fingers are moved relative to the remainder of the skin treatment device.

The skin treatment device includes electronic circuitry for applying a radiofrequency electromagnetic signal to a radiofrequency electrode that is incorporated into each mechanical finger. For example, radiofrequency electromagnetic signals of opposite polarity may be applied concurrently to two (or more) of the mechanical fingers. A frequency or amplitude (and thus a power) of the radiofrequency signal may be adjustable. The frequency, amplitude, or another characteristic of the radiofrequency signal may be generated so as to change in a periodic manner. For example, a variation of a characteristic of a radiofrequency signal that is applied to a mechanical finger may be coordinated with motion of the mechanical finger.

A skin treatment device in accordance with embodiments of the present invention may be portable. For example, components of the skin treatment device may be contained within a single housing. The housing may be of such a size as to enable the skin treatment device to be held in one hand. The skin treatment device may be shaped so as to be securely and comfortably held in the hand.

A skin treatment device in accordance with embodiments of the present invention may be placed in contact with skin and operated. For example, a user of the device may hold the skin treatment device such that the mechanical fingers are placed in contact with the user's own skin, or with the skin of another person whose skin is being treated by the user. Operation of the skin treatment device may include moving the mechanical fingers while concurrently applying a radiofrequency electromagnetic signal to the mechanical fingers.

Mechanical movement of the mechanical fingers may massage the skin to which the skin treatment device is applied. For example, the mechanical fingers may be move in a periodic back-and-forth motion toward and away from each other. The periodic back-and-forth motion may then alternately squeeze (pinch) and stretch the skin that is between the mechanical fingers. Movement of the mechanical fingers may be configured so as to assure that the resulting massaging is enjoyable or tolerable, without causing any pain or discomfort (e.g. by applying an excessive force to the skin). The user may manually adjust the force with which the skin treatment device is pressed against the skin being treated.

Concurrent application of the radiofrequency electromagnetic signal to the skin may cause a radiofrequency electrical current to flow through the skin. The flow of radiofrequency electrical current through the skin may then heat the skin (electro-thermolysis of the skin).

The depth at which a radiofrequency electrical current flows below the outer surface of the skin may be determined by one or more factors. The factors may include, for example, the frequency of the applied radiofrequency electromagnetic signal, the temperature of the skin, the conductivity of the skin, and a separation distance between the electrodes (each electrode at a distal end of one of the mechanical fingers, or being identical with an outer surface of a mechanical finger) through which the radiofrequency electromagnetic signal is applied to the skin. A motion of the mechanical fingers in which the distal ends of two mechanical fingers alternately approach and retreat from one another causes the separation distance between the electrodes to increase and decrease during the motion. The increase and decrease of the separation distance may thus vary the depth of radiofrequency electrical current, and thus of heating (electro-thermolysis), within the skin. Thus, the application of a radiofrequency electromagnetic signal to the skin concurrently with a back-and-forth motion of the electrodes may enable repetitive heating of layers within the skin at a range of depths.

Control of the frequency of the applied radiofrequency electromagnetic signal during the course of the back-and-forth motion of the mechanical fingers may enable further control of the depth of the heating. For example, the frequency of the applied radiofrequency electromagnetic signal may be coordinated with the back-and-forth motion of the mechanical fingers such that radiofrequency electrical current flows at an approximately constant depth. In this case, the skin may be heated at an approximately constant depth throughout the back-and-forth motion of the mechanical fingers. As another example, the frequency of the applied radiofrequency electromagnetic signal may be coordinated with the back-and-forth motion of the mechanical fingers so as to increase the range of depths through which the radiofrequency electrical current flows. Thus, a range of depths at which the skin is heated may be further increased.

One or more of the mechanical fingers may be provided with a temperature sensor. The temperature sensor may be placed in thermal contact with the skin when the skin treatment device or the mechanical fingers of the skin treatment device are placed in contact with the skin. The temperature sensor may generate a voltage or other electrical signal that is indicative of a measured temperature of the skin. In some embodiments, each of the mechanical fingers may be provided with a temperature sensor. Each of the temperature sensor sense temperature of the skin at the corresponding point of contact of the finger with the skin, simultaneously when the finger conducts radiofrequency electromagnetic signal to the point of contact.

Circuitry or a controller for controlling generation of the radiofrequency electromagnetic signal may be coupled to the temperature sensor. The circuitry may be configured such that if a signal that is generated by the temperature sensor indicates that the skin has been warmed beyond a predetermined threshold value, generation of the radiofrequency electromagnetic signal is interrupted (e.g. stopped or continued with smaller amplitude).

A skin treatment device in accordance with embodiments of the present invention may be configured for home use or for use by a nonprofessional user. For example, the skin treatment device may be sufficiently small so to enable storage of the skin treatment device in a similar manner to other home cosmetic or beauty products and devices. Also, a small size and an ergonomic shape of the skin treatment device may enable the skin treatment device to be handled and operated without the assistance of any fixtures or other support structure. The skin treatment device may include built-in safety features that enable safe operation by a nonprofessional user. In accordance with some of the embodiments, the device includes a flexible sleeve to prevent exposure of the skin to the circuitry of the device. The flexible sleeve seals a space between the fingers and the housing, and receives the pinched skin within a depression thereof to avoid contact of the pinched skin with any of the internal components of the device, while not interfering the movement of the mechanical fingers. Thus, rendering the device suitable for a safe and secure use by a nonprofessional user.

Treatment of skin using a skin treatment device in accordance with embodiments of the present invention may be advantageous. A skin treatment device as described herein may be continually slid or glided over the skin surface concurrently with operation of the skin treatment device (e.g. while concurrently applying a radiofrequency electromagnetic signal to the skin and massaging the skin). On the other hand, some previously described skin treatment devices utilize a vacuum to attach to or grab a region of skin to be treated. With such a previously described device, it would be necessary to break the vacuum before moving the device to another region of the skin. Thus, it would not be possible to move such a previously described device over skin during use.

Figure 1:
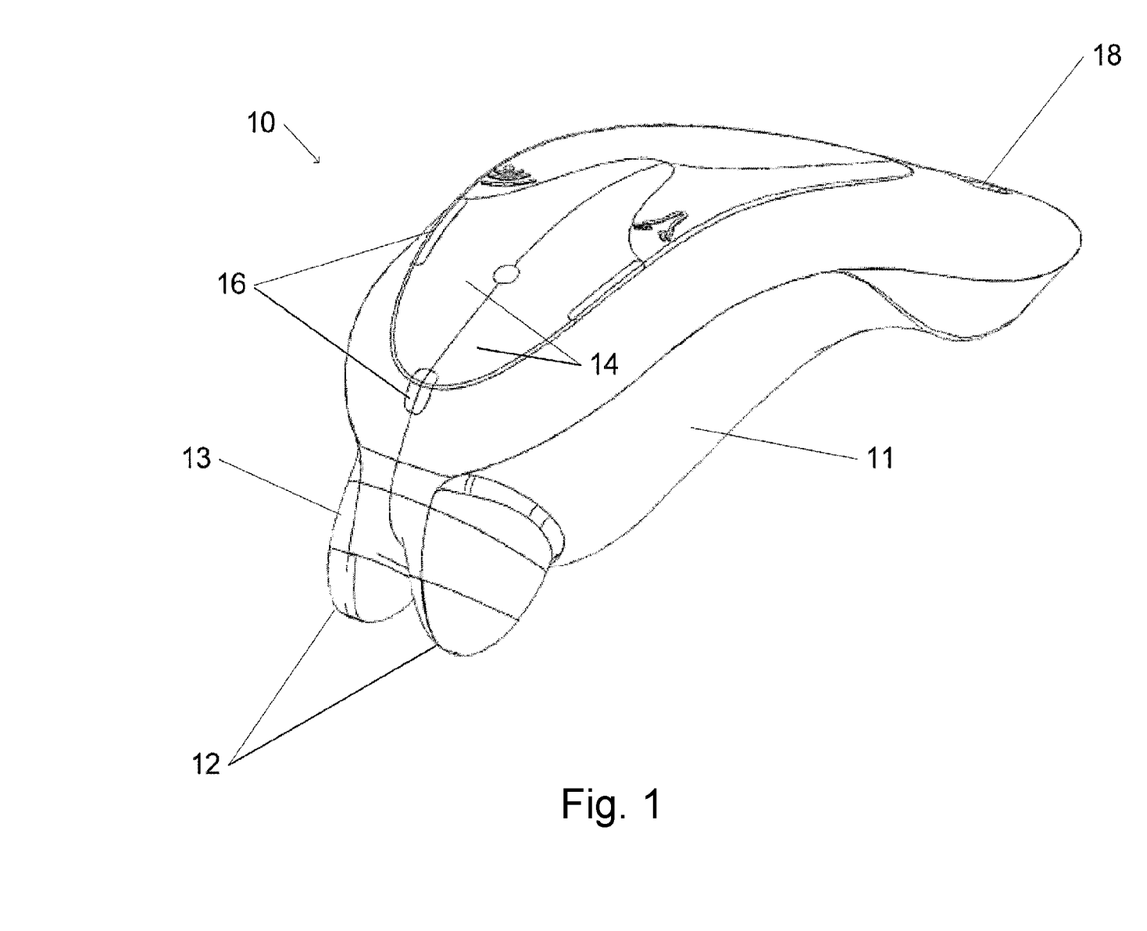
FIG. 1 shows a skin treatment device in accordance with an embodiment of the present invention.

FIG. 1 shows a skin treatment device in accordance with an embodiment of the present invention.

Skin treatment device 10 is enclosed within housing 11. Housing 11 may be configured with an ergonomic shape so as to enable skin treatment device 10 to be held in a single hand by a user. The shape of housing 11 may be configured so as to enable holding or pressing mechanical fingers 12 against the skin to be treated. The shape of housing 11 may also enable convenient and effective manipulation of skin treatment device 10. Housing 11 may include a rigid electrically insulating material (e.g. plastic) so as to electrically and mechanically isolate a user of skin treatment device 10 from any internal electrical or mechanical components of skin treatment device 10. Housing 11 may be designed to prevent isolate internal components of skin treatment device 10 from environmental factors (e.g. moisture or corrosive materials) that may adversely affect operation of the internal components.

Mechanical fingers 12 extend from an end of skin treatment device 10 that is configured to be placed against the skin to be treated. Mechanical fingers 12 are configured to move in a coordinated motion alternately toward and away from one another. Thus, when placed against skin, the coordinated motion of mechanical fingers 12 may result in a gentle pinching and releasing of a region of skin between mechanical fingers 12. Thus, the skin may be massaged by the motion of mechanical fingers 12.

Each mechanical finger 12 may be contoured (e.g. without sharp edges or corners) so as to prevent scratching of the skin or to slip over the skin. A surface of the mechanical finger 12 may be ridged, embossed, pitted, or otherwise patterned so as to facilitate grabbing or gripping the skin.

A material for an outer surface of each mechanical finger 12 may be selected so as to avoid irritation or chafing of the skin. Prior to or during use, a lubricating (e.g. an electrically conducting) fluid, gel, or cream may be applied to each mechanical finger 12.

Flexible sleeve 13 (explained in detail with reference to FIG. 5 below) of the device 10 may be made of a flexible material, such as flexible plastic or rubber. The flexibility of flexible sleeve 13 may enable housing 11 to remain sealed while enabling motion of mechanical fingers 12.

In the illustrated embodiment, skin treatment device 10 includes two mechanical fingers 12. In other embodiments, more than two mechanical fingers may be included. For example, a plurality of mechanical fingers may be arranged in cooperating pairs. The mechanical fingers of each cooperating pair may move in a coordinated motion. In other embodiments, three or more mechanical fingers may be placed in a single row and caused to move with a coordinated motion. For example, a mechanical finger that is located between two neighboring mechanical fingers may alternately move toward one of the neighboring mechanical fingers and then toward the other. The neighboring mechanical fingers may be stationary or moveable.

Part or all of an outer surface of each mechanical finger 12 may include, or may be made of, a conducting material. For example, the conducting material may include a metal, a conducting plastic, or another conducting material suitable for inclusion in an outer surface of mechanical finger 12. Inclusion of the conducting material may facilitate electrical coupling of the mechanical finger 12 to the skin to be treated.

Skin treatment device 10 may include one or more controls 14. For example, controls may include one or more pushbuttons (as shown), switches, levers, dial wheels, or knobs. A user may operate a control 14 so as to control operation of skin treatment device 10. For example, operation of a control 14 may cause skin treatment device 10 to be powered on or off, or to enter a standby status. Operation of control 14 may indicate selection of a mode of operation of skin treatment device 10.

Operation of a control 14 may start or stop motion of mechanical fingers 12. Operation of a control 14 may change or select a speed, distance (e.g. amplitude) or other characteristic of the motion. For example, operation of a control 14 in the form of a pushbutton may change a state of motion of mechanical fingers 12 from one state to a successive state in accordance with a predetermined sequence of states. As another example, control 14 may be operated to select a characteristic of the motion from among a set of predetermined characteristics.

Operation of a control 14 may initiate or stop generation of a radiofrequency electromagnetic signal for conduction into the skin by mechanical fingers 12. Operation of a control 14 may cause resumption of generation of radiofrequency electromagnetic signal after an interruption, e.g. as caused in response to a detected high skin temperature. Operation of a control 14 may change a frequency, amplitude, or other characteristic of a radiofrequency electromagnetic signal that is applied to mechanical fingers 12. For example, successive operation of a control 14 may cause one or more characteristics of the radiofrequency electromagnetic signal to change in accordance with a predetermined sequence of signal characteristics.

Skin treatment device 10 may include one or more indicators 16. For example, an indicator 16 may include a light-emitting or other visible indication of a status of skin treatment device 10. Indicator 16 may include a light emitting diode (LED), light bulb, or other light generating device placed on or near the surface of skin treatment device 10 or housing 11 (e.g. protected by or enclosed in a transparent or translucent window, dome, or casing). Indicator 16 may include a light emitting device (e.g. light bulb or LED) that is located interior to skin treatment device 10, with its light being channelled to an outer surface of skin treatment device 10 or housing 11 (e.g. by an optical fiber or other light guide). For example, one or more indicators 16 may indicate a power state of skin treatment device 10 (e.g. power on, power off, standby).

One or more indicators 16 may indicate a current motion state of mechanical fingers 12. A motion state may include, for example, the motion being on or off, a speed, amplitude, or other characteristic of motion, or a currently selected motion state from among a limited set of predetermined motion states.

One or more indicators 16 may indicate a current state of a radiofrequency electromagnetic signal motion that is currently applied by mechanical fingers 12. A state of an applied radiofrequency electromagnetic signal may include, for example, whether signal generation is currently turned on or off, a frequency, amplitude, or other characteristic of the signal, or whether current generation has been interrupted (e.g. due to detected high skin temperature).

In addition to, or in place of, a visible indication, skin treatment device 10 may be configured to generate an audible signal to indicate a current state of, or a change in a current state of, skin treatment device 10.

Skin treatment device 10 may include one or more connectors 18. A connector 18 may be configured to connect to a corresponding connector of an appropriate cable.

For example, a connector 18 may be configured to enable connection of skin treatment device 10 to an external power source (e.g. electric mains or power grid, or a power adapter, converter, or transformer) via an appropriate power cable. In accordance with some embodiments of a skin treatment device 10, skin treatment device 10 may incorporate an internal power source. For example an internal power source may include a replaceable of rechargeable battery or cell. A rechargeable battery may be recharged by connecting an appropriate connector 18 to an external power source. In other embodiments, power to operate skin treatment device 10 is provided solely by an external power source that is connected to a connector 18.

A connector 18 may be configured to connect an incorporated processor of skin treatment device 10 to a data port of an external computer, controller, or other device. Such a data connection may enable, for example, configuration of skin treatment device 10. In such a case, parameters for operation of skin treatment device 10 may be set or modified by a user or external device. In this manner, a skin treatment device 10 may be configured in accordance with, e.g., preferences of a user, or in accordance with changing manufacturer's recommendations (e.g. particular motion protocols for motion of mechanical fingers 12, or for generation of particular radiofrequency electromagnetic signals). Such a data connection may also facilitate diagnosis of problems with operation of a skin treatment device 10.

Figure 2:
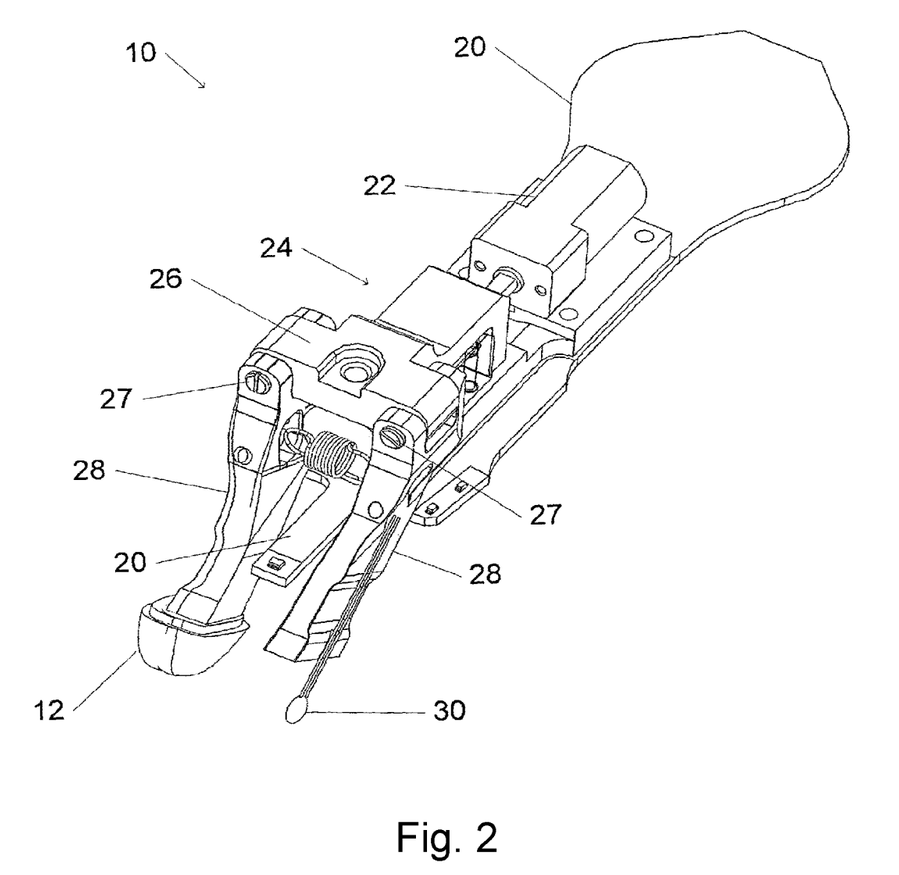
FIG. 2 shows internal components of the skin treatment device shown in FIG. 1.

FIG. 2 shows internal components of the skin treatment device shown in FIG. 1. In FIG. 2, some of the components are shown schematically.

The electrical system 20 of skin treatment device 10 is represented schematically by a printed circuit board. Electrical system 20 may be considered to represent all internal electrical and electronic circuitry and components of skin treatment device 10.

Figure 3:
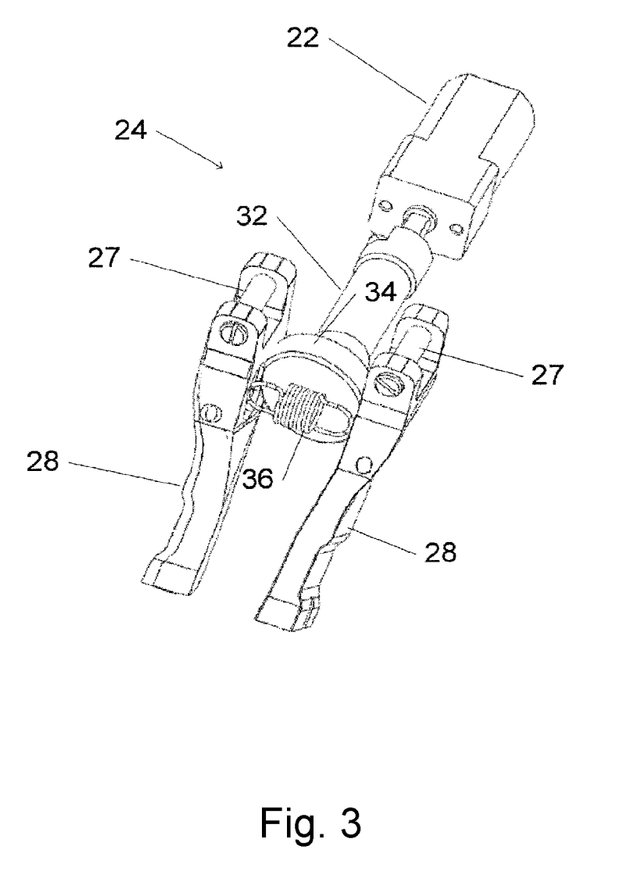
FIG. 3 shows a transmission for moving a mechanical finger of a skin treatment device, in accordance with an embodiment of the present invention.

FIG. 3 shows a transmission for moving a mechanical finger of a skin treatment device, and described in detail further below.

Figure 4:
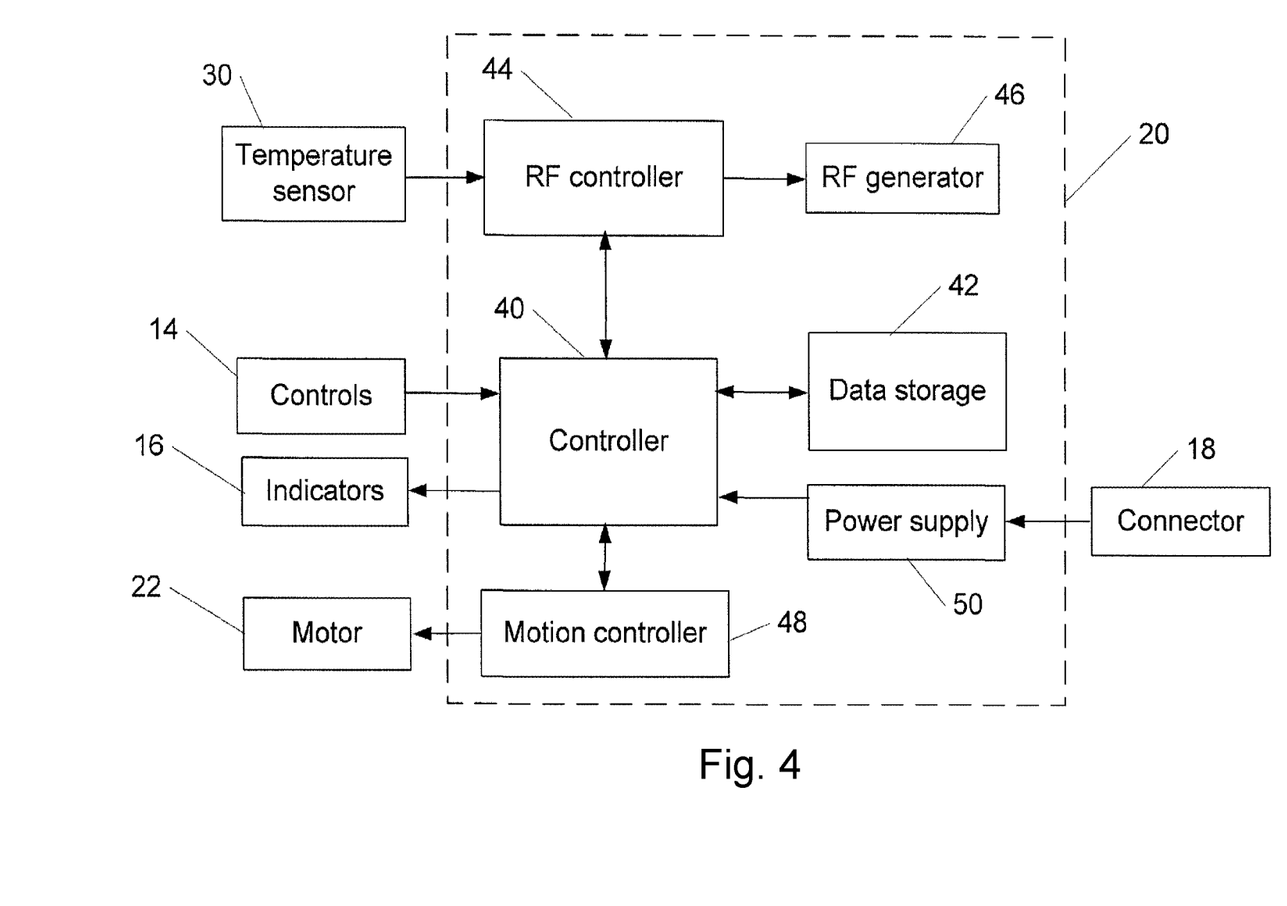
FIG. 4 is a block diagram of an electrical system of operation of a skin treatment device in accordance with embodiments of the present invention.

FIG. 4 is a block diagram of an electrical system for operation of a skin treatment device in accordance with embodiments of the present invention.

Electrical system 20 may include a controller 40 for controlling operation of skin treatment device 10. For example, the controller may include a controller 40. Controller 40 may represent a unit, or a plurality of intercommunicating units, that is configured to coordinate among various components of electrical system 20. Controller 40 may include one or more processors that are configured to operate in accordance with programmed instructions. In another example, controller 40 may include circuitry (e.g. in the form of an integrated control circuit) that is configured to operate components of skin treatment device 10.

Controller 40 may communicate with a data storage unit 42. Data storage unit 42 may include one or more volatile or non-volatile data storage devices, or may represent a data storage function of a device. For example, data storage unit 42 may include a non-volatile data storage device for storing programmed instructions or data for operation of a skin treatment device in accordance with some embodiments of the present invention. Data storage unit 42 may be used to store data that is generated during operation of the skin treatment device by a controller 40 in the form of processor.

Controller 40 may be configured to detect operation of a control 14. Controller 40 may operate in accordance with a detected operation of one or more controls 14 by a user.

Controller 40 may be configured to operate an indicator 16. For example, an indicator 16 may be operated to indicate a current state or status of operation of controller 40 or a component of electrical system 20.

Controller 40 may communicate with components and circuitry of generating a radiofrequency electromagnetic signal. Radiofrequency (RF) controller 44 may control generation of a radiofrequency electromagnetic signal. Radiofrequency controller 44 may represent one or more components or modules of controller 40, may include components that are separate from controller 40, or both. Radiofrequency controller 44 may be configured to select a radiofrequency electromagnetic signal to be generated by radiofrequency generator 46. A radiofrequency electromagnetic signal that is generated by radiofrequency generator 46 may be conducted to one or more mechanical arms 28, or to a conducting element that is incorporated into a mechanical arm 28. Mechanical arms 28 may conduct the generated radiofrequency electromagnetic signal to each mechanical finger 12. The generated radiofrequency electromagnetic signal may induce a radiofrequency electrical current to flow in skin that is in contact with mechanical fingers 12.

Radiofrequency controller 44 may select a radiofrequency electromagnetic signal on the basis of an indication based on operation by a user of a control 14. Generation of a radiofrequency electromagnetic signal may be controlled in accordance with a skin temperature that is sensed by temperature sensor 30. For example, if a sensed temperature is above a threshold temperature value, radiofrequency controller 44 may stop generation of a radiofrequency electromagnetic signal by radiofrequency generator 46.

Controller 40 may communicate with components and circuitry for controlling motion of moving components, such as mechanical fingers 12. Motion controller 48 may be configured to operate motor 22. For example, motion controller 48 may be configured to adjust an electrical current that is provided to drive motor 22 so as to operate drive motor 22 at a particular speed. Operation of drive motor 22 may cause mechanical fingers 12 to move in a predetermined manner.

Motion controller 48 may be configured to monitor an electrical current that is supplied to drive motor 22. For example, monitoring a current that is supplied to drive motor 22 may enable detecting a state where motion of a mechanical arm 28 or a mechanical finger 12 is impeded or obstructed.

Controller 40 may be configured to operate motion controller 48 in coordination with radiofrequency controller 44. For example, operation of motion controller 48 may be coordinated with operation of radiofrequency controller 44 so as to generate a radiofrequency electromagnetic signal that depends on a current configuration of (e.g. separation distance between) mechanical fingers 12. For example, drive motor 22 or one or more components of transmission 24 may be provided with an encoder or other sensing device for sensing a current orientation or position of a mechanical arm 28 (e.g. derived from an sensed orientation of a cam 34). Coordination of operation of motion controller 48 with radiofrequency controller 44 may enable control of a depth at which a radiofrequency electrical current flows through the skin or underlying tissue.

Electrical system 20 may include a power supply 50. Power supply 50 may provide power for operation of controller 40 or for operation of another component of electrical system 20. Power supply 50 may include a replaceable or rechargeable power source, such as a replaceable or rechargeable battery or cell. Power supply 50 may connect to an external power source, such as an electric power grid, generator, or power supply device, via connector 18. Power supply 50 may include an appropriate converter or transformer for converting an input electrical current from connector 18 to a current that is usable in operating one or more components of the skin treatment device.

Electrical system 20 may connect to or communicate with one or more temperature sensors 30. A temperature sensor 30 may be mounted on a mechanical arm 28. Temperature sensor 30 may be embedded within, or may be in thermal contact with, a mechanical finger 12 that is placed at a distal end of mechanical arm 28. In some embodiments, a temperature sensor 30 may be provided in each of the mechanical fingers. Each temperature sensor 30 may sense the temperature of the skin at the respective contact point of the corresponding finger 12 with the skin. Thus, the temperature sensor 30 is configured to sense the temperature of the skin at the point of contact where the electromagnetic radio frequency signal is provided to the skin, thereby ensuring better accuracy in sensing temperature of the skin at the contact points receiving the electromagnetic radio frequency signal, and more efficient and effective operation of the device.

Operation of drive motor 22 may cause motion of a mechanical finger 12. For example, a rotational motion of drive motor 22 may be converted by a transmission 24 to a back-and-forth motion of one or more mechanical arms 28. A mechanical arm 28 may be mounted to arm base 26 via an axis 27. Mechanical arm 28 may thus rotate about axis 27 relative to arm base 26. Thus, operation of drive motor 22 and transmission 24 may cause a mechanical finger 12 at a distal end of a mechanical arm 28 to rotate with a back-and-forth motion about axis 27.

FIG. 3 shows a transmission for moving a mechanical finger of a skin treatment device, in accordance with an embodiment of the present invention.

Drive motor 22 is coupled to drive shaft 32 of transmission 24. Thus, a torque that is produced by operation of drive motor 22 may rotate drive shaft 32. An end of drive shaft 32 that is distal to drive motor 22 is coupled to cam 34 of transmission 24. Thus, rotation of drive shaft 32 causes cam 34 to rotate.

Mechanical arms 28 are mounted to arm base 26 (shown in FIG. 2) via axes 27. Thus, a mechanical arm 28 may be made to rotate about its axis 27. Mechanical arms 28 are connected to one another by spring 36. Spring 36 may provide an inward restoring force or torque when one mechanical arm 28 is rotated away from the other.

Cam 34 is placed between mechanical arms 28. Cam 34 thus counters the inward torque that is exerted by spring 36 so as to separate one mechanical arm 28 from the other. Cam 34 has an elliptical shape. Thus, rotation of cam 34 continually changes the distance of separation between one mechanical arm 28 and the other. For example, when cam 34 is rotated such that the major axis of the elliptical shape separates mechanical arms 28, the separation distance between mechanical fingers 12 (FIG. 1) from one another is close to its maximum. On the other hand, when cam 34 is rotated such that the minor axis of the elliptical shape separates mechanical arms 28, the separation distance between mechanical fingers 12 is close to its minimum.

Spring 36 may be selected or configured so as to limit a maximum inward force that may be exerted by spring 36 on mechanical arms 28. The force limit may be selected or configured such that the maximum force is too weak to cause any pain (such as painful pinching) or damage to any skin that may be positioned between mechanical fingers 12.

In the configuration shown in FIGS. 2 and 4, the motion of both mechanical arms 28 and of both mechanical fingers 12 is symmetric and opposite. Other configurations in which the mechanical fingers move in an asymmetric manner are possible.

Although both mechanical arms in FIG. 3 are shown as rotatable about their respective axes 27, other configurations are possible. For example, one mechanical arm may be rotatable, while the other is stationary. As another example, each mechanical arm may be moved, but in a nonsymmetrical manner. For example, as an alternative to a single symmetrically mounted elliptically-shaped cam 34, each mechanical arm may be operated by a separate cam, or by a shared cam with an asymmetric shape, or by a cam with a symmetric shape that is mounted eccentrically on its axis of rotation. A restoring force may be separately provided to each mechanical arm. For example, a separate spring or piston connecting each mechanical arm to a stationary element of the skin treatment device may provide a separate restoring force to each of the mechanical arms.

Adjustment of a speed of operation of motor 22 may adjust a speed with which mechanical arms 28 and mechanical fingers 12 are moved.

A mechanism may be provided to adjust an amplitude or other distance of motion of a mechanical arm 28 or a mechanical finger 12. For example, a distance between axes 27 may be adjustable. A mechanism may be provided (e.g. manual or motorized) for changing a distance between axes 27.

In some embodiments of the present invention, a length of a mechanical arm 28 or a mechanical finger 12 may be adjustable. An attachment point of mechanical arm 28 to an axis 27, or of mechanical finger 12 to mechanical arm 28 may be adjustable (e g manually detachable and re-attachable). Mechanical arm 28 may be constructed with two or more telescoping sections so as to enable adjustment of the length of mechanical arm 28.

In some embodiments of the present invention, a transmission with a rotating cam may be configured such that lateral translation of the cam causes an amplitude of a motion of a mechanical arm to change. (A separate motor or transmission may be provided to effect or enable such motion.) For example, adjustment of a distance between an axis of rotation of the cam and the axes of the mechanical arms may adjust an amplitude of the motion of the mechanical arms. In another example, a cam may be in the form of a frustum of a cone (e.g. of an elliptical cone) or of a stepped cone. In this case, translating the cam along, or parallel to, the cams axis of rotation may cause the dimensions of the section of the cam that lies between the mechanical arms to change. Changing dimensions of the section of the cam between the mechanical arms may adjust the amplitude of the motion of the mechanical arms and of the attached mechanical fingers.

Figure 5:
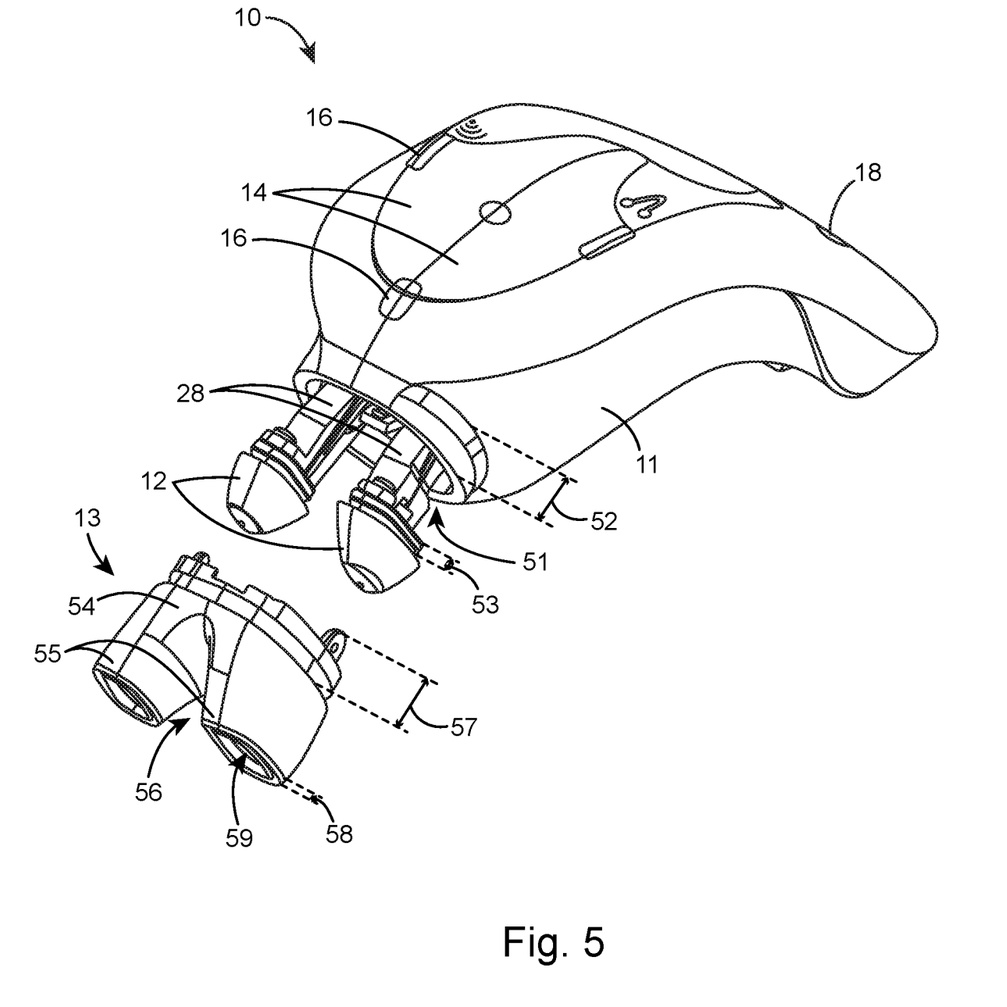
FIG. 5 shows an exploded view of the device shown in FIG. 1 depicting the configuration of a flexible sleeve with the device, in accordance with an embodiment of the present invention.

FIG. 5 shows an exploded view of the device shown in FIG. 1, depicting the configuration of a flexible sleeve with the device, in accordance with an embodiment of the present invention.

In the illustrated embodiment as shown in FIG. 5, the housing 11 of the device 10 includes an opening 51 having, on its periphery, a connection portion 52. Each of the mechanical fingers 12, at its respective periphery, includes a sleeve connection portion 53. The flexible sleeve 13 includes a waist portion 54, two leg portions 55, and a depression 56 between the two leg portions 55. The waist portion 54 includes a housing connection portion 57 that corresponds to the connection portion 52 of the housing 11. Each of the leg portions 55 include a finger connection portion 58 that corresponds to the respective sleeve connection portion 53 of the mechanical fingers 12. The connection portion 52, the housing connection portion 57, the sleeve connections portions 53, and the finger connection portions 58 may include any of the suitable means of connections as would be known to a person skilled in the art such as, but not limited to, screw-hole, snap fit, nut-bolt, depression-protrusion/projection, adhesive fixations, and any combinations thereof. In an embodiment, the waist portion 54 and the leg portions 55 may be integrally formed, while in a different embodiment, the waist portion 54 and the leg portions 55 may be separate elements articulated to each other. It is to be further understood herein that the number of leg portions 55 corresponds to the number of mechanical arms 28, in that, in the embodiments including more than two mechanical arms 28, there would be same number of leg portions 55 as of the mechanical arms 28.

In a ready-to-use state (for example, as the one shown in FIG. 1), the housing connection portion 57 is connected to the connection portion 52, and each of the finger connection portions 58 is connected to the respective sleeve connection portion 53. In the present example, an outer surface of the flexible sleeve 13, an outer surface of the mechanical fingers 12, and an outer surface of the housing 11 form a continuous surface. Each of the connections being such that the flexible sleeve 13 seals the space between the mechanical fingers 12 and the opening 51 of the housing 11. The configuration of the flexible sleeve 13 with the housing 11 and the mechanical fingers 12 is such that the leg portions 55 meet each other in a space between the mechanical arms 28 thereby forming the depression 56 in that space. Each of the leg portions 55 at least partially surrounds a respective mechanical arm 28. In an embodiment, each of the leg portion 55 may define a hollow 59 and a respective arm 28 may pass through that hollow 59. In the illustrated embodiment depicting the ready-to-use state (for example, as the one shown in FIG. 1), the housing connection portion 57 is shown to be connected to an inner surface of the connection portion 52, and the finger connection portions 58 are shown to be connected to outer surfaces of the sleeve connection portions 53. However, in different embodiments, variations and modification in such connections would fall within the scope of the present invention.

The material, the structural configuration, and the arrangement of the flexible sleeve 13 with the housing 11 enables the leg portions 55 to move along with the respective mechanical arm 28, and deform the flexible sleeve 13 accordingly to change at least one dimension (for example, depth, width, volume, etc.) of the depression 56. When the device 10 is in operation of massaging the skin, the movement of the two mechanical arms 28 causes the mechanical fingers 12 to pinch the skin. The flexible sleeve 13, sealing the space between the housing 11 and the mechanical fingers 12, prevents the pinched skin to come in contact with any internal component of the device 10, especially the electrical components and the mechanical arms 28. Furthermore, the depression 56 receives the pinched skin thereby offering a soft, smooth and comfortable feel to the skin, along with limiting the advancement of the pinched skin towards an interior of the housing 11, and all this without interfering with the movement of the mechanical arms 28. Thus, the material, structural configuration, and arrangement of the flexible sleeve enables a non-professional user to safely use the device 10.

A skin treatment method in accordance with embodiments of the present invention may include operation of a skin treatment device in accordance with embodiments of the present invention.

In accordance with the treatment method, at least two mechanical fingers of the skin treatment device are placed in contact with skin that is to be treated. A motor of the skin treatment device may be operated so as to continuously move (to be understood as including a sequence of intermittent movements) at least one of the mechanical fingers relative to the other. As a result of the motion, a separation distance between the mechanical fingers is continuously changed. The relative motion of mechanical fingers may massage the skin.

Concurrently with the motion, a radiofrequency generator may be operated so as to generate a radiofrequency electromagnetic signal that is conducted to the two mechanical fingers. A radiofrequency electrical current may thus be conducted by the skin from one of the mechanical fingers to the other. The depth at which the current is conducted through the skin may be affected by the separation distance between the mechanical fingers. As a result of the current, the skin near the conduction depth may be heated.

Thus, if characteristics of the generated radiofrequency electromagnetic signal, the depth of the current may change as a result of the motion of the mechanical fingers. Alternatively, one or more characteristics (e.g. a frequency) of the generated radiofrequency electromagnetic signal may be changed in coordination with the motion of the mechanical fingers. Such coordinated generation of the radiofrequency electromagnetic signal may be applied so as to exert precise control over heating of layers of the skin at different depths.

The invention claimed is:

1. A device, comprising:
   a housing comprising an opening, a periphery of the opening comprising a connection portion, wherein the housing encloses a generator for generating a radiofrequency electromagnetic signal and a controller for controlling the generator;
   two mechanical arms having a space therebetween, each of the two mechanical arms comprising a respective distal end projecting outwards from the opening of the housing, wherein the two mechanical arms are rotatable to change a separation distance between the distal ends of the two mechanical arms between a maximal separation distance and a minimal separation distance, a first one of the two mechanical arms being rotatable about a first rotation axis and a second one of the two mechanical arms being rotatable about a second rotation axis laterally spaced from the first rotation axis, the two mechanical arms configured to rotate periodically back-and-forth about the respective first and second rotation axis thereof so that distal ends thereof move along an arcuate path;
   two mechanical fingers, each located at the distal end of a respective one of the two mechanical arms, a respective periphery of each of the two mechanical fingers comprising a sleeve connection portion, wherein each of the two mechanical fingers is configured to conduct the generated radiofrequency electromagnetic signal to a skin surface in contact with the two mechanical fingers, wherein at least one of the two mechanical fingers includes a temperature sensor to sense a temperature of the skin surface; and
   a flexible sleeve comprising a waist portion, two leg portions extending from the waist portion, and a depression between the two leg portions, the waist portion comprising a housing connection portion corresponding to the connection portion of the opening of the housing and connected thereto, each of the two leg portions comprising a through-opening, each of said two mechanical fingers extending through and from a corresponding one of said through-openings and is configured to contact the skin surface while being connected to the corresponding mechanical arm through the through-opening, and wherein each of the two leg portions at least partially surrounds a respective mechanical arm and the two leg portions meet each other in the space between the two mechanical arms, thereby forming the depression.

2. The device of claim 1, wherein each of the two mechanical fingers includes a respective temperature sensor to sense the temperature of the skin surface at the corresponding contact point of the mechanical finger with the skin, simultaneously while the mechanical fingers conduct the generated radiofrequency electromagnetic signal to the contact points.

3. The device of claim 1, wherein the device is shaped so as to be held by a single hand.

4. The device of claim 1, further comprising a motor and a transmission for rotating said at least one of the two mechanical arms.

5. The device of claim 4, wherein the transmission comprises a cam that is rotatable by the motor for changing the separation distance between the distal ends of the two mechanical arms.

6. The device of claim 5, wherein the cam is located so as to contact each of the two mechanical arms at a point between the distal end of the mechanical arm and the rotation axis of the mechanical arm.

7. The device of claim 5, further comprising a spring for exerting an inward torque on at least one of the two mechanical arms.

8. The device of claim 3, wherein said controller is configured for controlling operation of the motor.

9. The device of claim 1, wherein the radiofrequency electromagnetic signal is generated in accordance with the sensed temperature.

10. The device of claim 8, wherein the device is configured to interrupt the generation of the radiofrequency electromagnetic signal if the sensed temperature exceeds a threshold temperature.

11. The device of claim 1, further comprising a control for operation by a user.

12. The device of claim 1, further comprising an indicator for indicating a status of the device.

13. The device of claim 1, further comprising a power supply.

14. The device of claim 1, wherein each leg portion moves along with the respective mechanical arm, thereby at least partially deforming the flexible sleeve and changing at least one dimension of the depression.

15. The device of claim 1, wherein the flexible sleeve is configured to seal a space between the mechanical fingers and the opening of the housing.

16. The device of claim 1, wherein the leg portions and the waist portion are integrally formed.

17. The device of claim 1, wherein the leg portions and the waist portion are different elements articulated to each other.

18. The device of claim 1, wherein the leg portions define respective hollows and the respective mechanical arms pass therethrough.

19. The device of claim 1, wherein an outer surface of the flexible sleeve forms a continuous surface along with an outer surface of the housing and outer surfaces of the two mechanical fingers.

20. The device of claim 1, wherein the generator is configured to continuously vary a frequency of the radiofrequency electromagnetic signal in coordination with the changing separation distance.

* * * * *